(12) United States Patent
Hesels et al.

(10) Patent No.: US 10,444,306 B2
(45) Date of Patent: Oct. 15, 2019

(54) MAGNETIC RESONANCE FACILITY

(71) Applicants: Katharina Hesels, Erlangen (DE); Stefan Röll, Hirschaid (DE)

(72) Inventors: Katharina Hesels, Erlangen (DE); Stefan Röll, Hirschaid (DE)

(73) Assignee: Siemens Healthcare GmbH, Erlangen (DE)

(*) Notice: Subject to any disclaimer, the term of this patent is extended or adjusted under 35 U.S.C. 154(b) by 184 days.

(21) Appl. No.: 15/485,793

(22) Filed: Apr. 12, 2017

(65) Prior Publication Data

US 2017/0299669 A1 Oct. 19, 2017

(30) Foreign Application Priority Data

Apr. 14, 2016 (DE) .................. 10 2016 206 288

(51) Int. Cl.
| | |
|---|---|
| *G01V 3/00* | (2006.01) |
| *G01R 33/34* | (2006.01) |
| *G01R 33/30* | (2006.01) |
| *G01R 33/36* | (2006.01) |
| *A61B 5/055* | (2006.01) |
| *G01R 33/3415* | (2006.01) |

(52) U.S. Cl.
CPC ....... *G01R 33/34007* (2013.01); *G01R 33/30* (2013.01); *G01R 33/34084* (2013.01); *G01R 33/36* (2013.01); *A61B 5/0555* (2013.01); *G01R 33/3415* (2013.01); *G01R 33/3692* (2013.01)

(58) Field of Classification Search
CPC ..................................... G01R 33/30
USPC ................................. 324/318, 322
See application file for complete search history.

(56) References Cited

U.S. PATENT DOCUMENTS

| | | | |
|---|---|---|---|
| 5,400,787 A | 3/1995 | Marandos | |
| 6,762,606 B2* | 7/2004 | Jevtic | G01R 33/34046 |
| | | | 324/318 |
| 7,570,056 B2 | 8/2009 | Nakabayashi et al. | |

(Continued)

FOREIGN PATENT DOCUMENTS

| | | |
|---|---|---|
| JP | 2008173192 A | 7/2008 |
| JP | 2010051686 A | 3/2010 |

OTHER PUBLICATIONS

German Office Action for related German Application No. 10 2016 206 288.3 dated Dec. 22, 2016, with English Translation.

*Primary Examiner* — Louis M Arana
(74) *Attorney, Agent, or Firm* — Lempia Summerfield Katz LLC

(57) ABSTRACT

A magnetic resonance facility is provided. The magnetic resonance facility includes at least one object table configured to mount an object to be examined and at least one coil facility embodied separately from the object table, which includes at least one local coil and at least one connecting portion, which may be introduced into at least one recess of the object table and may be held there to hold the coil facility. The connecting portion in the recess is guided displaceably along a longitudinal direction of the recess between different positions in which it may be held. At least one coil-facility-side connecting device is arranged on the connecting portion and may establish an electrical connection for the power supply and/or for signal transmission between the coil facility and the object table and/or at least one optical connection for signal transmission between the coil facility and the object table.

15 Claims, 7 Drawing Sheets

(56) References Cited

U.S. PATENT DOCUMENTS

| | | | |
|---|---|---|---|
| 7,990,147 B2 * | 8/2011 | Driemel | G01R 33/3415 |
| | | | 324/309 |
| 2008/0136412 A1 | 6/2008 | Kato | |
| 2009/0009172 A1 | 1/2009 | Feld et al. | |
| 2014/0097844 A1 * | 4/2014 | Tomiha | G01R 33/3692 |
| | | | 324/321 |
| 2016/0054404 A1 * | 2/2016 | Duensing | G01R 33/34046 |
| | | | 324/309 |
| 2016/0195594 A1 * | 7/2016 | Leussler | G01R 33/34084 |
| | | | 600/422 |

* cited by examiner

MAGNETIC RESONANCE FACILITY

The application claims the benefit of German Patent Application No. DE 10 2016 206 288.3, filed Apr. 14, 2016, incorporated by reference in its entirety.

TECHNICAL FIELD

The disclosure relates to a magnetic resonance facility including at least one object table for mounting an object to be examined and at least one coil facility embodied separately from the object table including at least one local coil and at least one connecting portion that may be introduced into at least one recess of the object table and may be held there to hold the coil facility. The disclosure also relates to an object table and a coil facility for use in a magnetic resonance facility.

BACKGROUND

The use of local coils in magnetic resonance facilities is known for local reception of electromagnetic radiation emitted by an excited object to be examined. In the simplest case, such local coils may be arranged directly on an object to be examined. However, such an arrangement is relatively time-consuming and requires complicated cabling that, on the one hand, may disrupt the magnetic resonance scan and, on the other, requires complex screening to prevent the magnetic resonance scan from influencing the signal transmission.

To enable an easier arrangement of these local coils, the use of so-called "direct connect" coil supports is known. These include one or more local coils on a rigid support that may be arranged on the object table on a predefined position of an object table, which is in particular predetermined by a known patient geometry. In this case, table-side connecting elements are provided at the corresponding position and used for both the electrical and mechanical connection of the coil support. Such coil supports are known for head coils, back coils and ankle coils, for example.

The problem with this solution is that it is necessary to use different local coil facilities for each scan geometry. Moreover, many scans also require coils that may be used flexibly, which furthermore should be attached and cabled in the normal way. Therefore, the disclosure is based on the object of disclosing a magnetic resonance facility that connects a simple arrangement of local coils on the object to be examined with flexible arrangement options for these local coils.

SUMMARY AND DESCRIPTION

The scope of the present disclosure is defined solely by the appended claims and is not affected to any degree by the statements within this description. The present embodiments may obviate one or more of the drawbacks or limitations in the related art.

The object is achieved by a magnetic resonance facility of the type described in the introduction, wherein the connecting portion is guided displaceably in the recess along a longitudinal direction of the recess between different positions in which it may be held, wherein at least one coil-facility-side connecting device is arranged on the connecting portion, which, when the connecting portion is held in the recess, together with an object-table-side connecting device arranged in the recess, establishes an electrical connection for the power supply for the coil facility and/or for signal transmission between the coil facility and the object table and/or at least one optical connection for signal transmission between the coil facility and the object table.

According to the disclosure, the coil facility is guided displaceably in one or more recesses over the object table and may be held at a plurality of positions. This enables the arrangement of the coil facility and hence the local coil or local coils to be flexibly configured to the scanning task and the object to be examined. When the coil facility is held in each of these positions, at least one electrical and/or optical connection is established automatically by the object-table-side and the coil-facility-side connecting facility, and it is also possible completely or to a large extent to dispense with additional cabling for the local coils. In particular, the scan signals from the local coil or the local coils may be transmitted by this optical or electrical connection. It is also possible for control signals for the coil facility, which may control amplifiers or multiplexing facilities integrated in the coil facility, to be transmitted by the electrical or optical connection. It is also possible to provide a power supply for components of the coil facility by an electrical connection.

These connection options reduce the amount of cabling in the immediate environment of the object to be examined or in the scanning region of the magnetic resonance facility. As explained in the introduction, it is possible to improve access to the object to be examined, reduce scan artifacts caused by the cabling, and to provide guidance of the signals or power supply that is less susceptible to errors. Sheath current filters that are required in some circumstances may be integrated directly into the object table. The object table may have one or more signal lines connecting the at least one object-table-side connecting device permanently or disconnectably to a control and/or scanning facility. These may be guided away in a region of the object table, which may be located outside the scanning region, and therefore the signal guidance in this region is less critical for the scanning quality and the signals are affected to a lesser degree by the magnetic fields of the magnetic resonance facility.

The recess may be embodied as a straight groove, in particular extending in a longitudinal direction of the object table. Hence, if the object to be examined has an oblong shape, for example a human, the groove may extend substantially parallel to a longitudinal axis of the object to be examined. The connecting portion may be guided in the recess in such a way that the connecting portion is guided non-rotatably and/or that, apart from the removal of the connecting portion from the recess, the sole degree of freedom of the connecting portion is displacement along the recess.

The coil facility may, at least partially, be rigid or elastic so that the holding of one or more connecting portions in one or more recesses enables the position of the coil facility to be defined. Hence, the holding of the connecting portion may define the position of the at least one local coil, wherein it is, however, possible for the position of the local coil with respect to the connecting portion to be selectively varied, for example, by supporting it on an air cushion. The coil facility may be held on the object table such that the coil facility may be additionally used to hold an object to be examined. For example, a patient may be fixed by the coil facility.

The dimensions of the recesses may be selected to prevent inadvertent ingress. The recesses may guide the connecting portions perpendicular to a surface of the object table or at an angle thereto, in particular inclined away from the object to be examined. A pair including an object-table-side and a coil-facility-side connecting facility or a plurality of pairs assigned to different connecting portions and/or recesses may be used to guide a plurality of signals to or from the coil facility by a plurality of connections. One or more of the connections may be used for the power supply for active components of the coil. It is also possible for at least one connection for a $B_0$ shim element to be provided to compensate local inhomogeneity of the $B_0$ field. It is possible for one or more connections for control signals to be provided, for example, to tune or detune individual local coils. Moreover, a plurality of connections for the reception of magnetic resonance signals, (e.g., screened against radio-frequency fields), may be provided. It is also possible for at least one connection to be provided to transmit radio-frequency signals via one of the local coils or an antenna embodied separately therefrom.

The coil facility may have up to 30 local coils. To reduce the number of connections and hence enable the use of low-complexity object-table-side and coil-facility-side connecting devices, it is possible for multiplexing of the incoming signals to be provided, wherein, for example, double, quadruple, or octupole multiplexing is possible. This enables the number of receive connections or receive lines to be reduced to four to eight. The complexity of the individual connecting devices may be further reduced if the coil facility is held by two or more connecting portions each having one connecting device so that the signal guidance may be divided between several of the connecting devices.

It is possible for connecting portions of different coil facilities to be accommodated in the same recess. In this case, they may also abut each other immediately. The coil facilities themselves or their local coils may be arranged on the object table such that, when viewed projected onto the object table, they overlap, at least partially. This enables the image quality of a magnetic resonance recording to be increased.

It is possible for parts of a communication between the coil facility and a scanning and/or control facility to take place by a radio device. In this case, the recess may be used purely for holding the coil facility and/or for holding and supplying power. It is however also possible for, in addition to the signals transmitted by radio, other parts of the signals to be transmitted via the connecting facilities.

The coil facilities may be embodied such that, together with the object table, they surround the object to be examined, in particular in a substantially annular shape. In this case, access windows may be provided in the coil facilities enabling access to the object to be examined, for example, to perform an intervention on a patient.

The recesses may be used to hold connecting elements for further facilities. The further facilities may be connected by a flexible connection to the respective connecting element so that the connecting element and the flexible connection may substantially function as cables for the further facility. This enables shorter cables and hence reduces disruption to the scan and provides better accessibility of the object to be examined to be achieved for further facilities.

The recess and the connecting portion may be embodied such that continuous displacement of the connecting portion in the recess is possible, wherein the connecting portion may be held at every position of this continuous displacement. Hence, this holding enables the establishment of the least one optical and/or electrical connection at every position of this continuous displacement.

The coil facility may be elastic and/or flexible and have a connecting portion on each of two opposite ends. The flexibility and the bilateral holding of the coil facility may enable the achievement of an arched or U-shape of the coil facility arranged on the object table. The inherent elasticity of the coil facility enables the coil facility to be held such that it does not lie on the object to be examined. As explained above, it may be advantageous when using a plurality of connecting portions to provide coil-facility-side connecting devices on both connecting portions so that the connections used for the coil facility may be distributed between the different connecting facilities.

The connecting portion may be held in the recess by a detachable latching connection. The holding may be achieved entirely by the detachable latching connection or it is possible for additional supportive measures to be provided, for example additional clamping of the connecting portion by further elements. A latching connection may be implemented in that the floor of a recess is embodied as a spring connector strip that is flexibly displaceable with respect to the walls of the connecting portion in an introducing facility. At least one side wall of the recess and the connecting portion may be provided with hook-shaped projections, which may be interlocked with one another. If these are arranged such that the spring connector strip presses the hook-shaped projection of the connecting portion into the hook-shaped projection of the side wall, the interaction of the hook-shaped projections and the spring connector strip may achieve a reliable latching connection that may be disconnected in that the connecting portion is pressed against the spring resistance of the spring connector strip further into the recess to disconnect the interlocking. A corresponding holding provides a user with reliable mechanical feedback that the coil facility is correctly positioned. Further measures such as those explained by way of example below may then be used to clamp the connecting portion to reduce play in the extension.

A pressure hose with an extension that may be varied by changing its filling pressure with a filling facility of the magnetic resonance facility may be arranged in the recess, wherein the connecting portion may be clamped in the recess by increasing the filling pressure. The filling facility may be controlled by a control facility of the magnetic resonance facility. It is, for example, possible, to fill or empty the pressure hose after the actuation of an operating element. Such clamping by a pressure hose may be used as the sole measure for holding the connecting portion. However, it is also possible to connect this clamping by a pressure hose with the above-described holding by a detachable latching connection. Clamping by a pressure hose thus reduces the mobility of the portion in the recess thus achieving a more reliable optical and/or electrical connection. This clamping also enables the provision of gas-tight connections that extend the functionality of the coil facility as explained below. The filling facility may fill the pressure hose with compressed ambient air or other gases.

The coil facility may include at least one gas cushion for fixing the object to be examined and/or for positioning the local coil, wherein the extension of the gas cushion may be varied by changing its filling pressure with a filling facility of the magnetic resonance facility. The filling facility may be the same filling facility as that used to adapt the filling pressure of the pressure hose or be embodied separately therefrom. The filling facility may be controlled by the control facility of the magnetic resonance facility to fill or empty the gas cushion, for example, following an operator input by a user. It is possible for a plurality of gas cushions to be provided and/or for the gas cushion to have plurality of chambers, wherein the plurality of gas cushions or the plurality of chambers may be at least partially filled in sequence, e.g., initially at least one of the gas cushions or at least one of the chambers may be filled up to a prespecified minimum pressure and then at least one further chamber or at least one further gas cushion filled. Such sequential filling is, for example, possible by non-return valves with a pre-specified counterforce. Sequential filling of the chambers or the gas cushion may take place such that initially chambers or cushions in a central region of the object to be examined may be inflated and then cushions or chambers in the edge region. This may enable controlled holding of the object to be examined or positioning of the local coils.

The gas cushion may be arranged between a support portion of the coil facility on the connecting portion and the local coil or at least one of the local coils so that the relative position of the local coil with respect to the support portion may be changed by changing the filling pressure of the gas cushion. The local coil or the local coils may be arranged on a side of the support portion facing the object table or the object to be examined so that filling the gas cushion enables them to be supplied to the object table and hence to the object to be examined and, in particular, applied to the object to be examined. In this case, the coil facility may be constructed in three layers, wherein the support portion establishes the outer layer facing away from the object table, which may be connected rigidly or elastically in a dimensionally stable way to the connecting portions. The gas cushions form an interim layer the extension of which may be varied by the degree of filling of the gas cushions. The inner layer is provided by the local coils or a layer supporting the local coils, which is in particular flexible.

A three-layer construction of this kind on the one hand enables the gas cushion to hold or support an object to be examined and on the other the local coil to be brought close to the object to be examined to optimize the quality of the scan data. Alternative embodiments with which the local coils are arranged permanently on the support portion, (e.g., between support portion and gas cushion), may, on the other hand, be simpler and cheaper to produce.

The gas cushion may be filled with gas through a filling opening, which is arranged on the connecting portion and, when the connecting portion is held in the recess, is connected in a gas-tight manner to an object-table-side gas feed through which the gas may be fed from the filling facility to the gas cushion. The gas feed may take the form of a plurality of separate gas feeds each used for the gas feed when the coil facility is held at a specific position or in a specific region gas feed. It is possible for one of the gas feeds to be selected automatically to feed gas to the gas cushion gas. To this end, it is possible to detect the position of the coil facility. However, it is however also possible for pressure sensors to be arranged in the individual gas feeds thus making it possible to identify the gas feed connected to the coil facility. Non-connected gas feeds may be separate from the gas supply. The provision of a pressure sensor in the gas feed also enables the pressure in the gas cushion to be determined close to the coil facility and hence with a high degree of precision. This enables a control facility of the magnetic resonance facility to define the filling pressure of the gas cushion precisely to enable optimal holding of the object to be examined or the local coils to be brought to the object to be examined.

In many of the embodiments, when gas cushions are filled by an object-table-side gas feed in the recess, pressurized gas, (e.g., compressed air), is available in the recess. This may be used in a service mode of the magnetic resonance facility to purge or clean the recess. This enables the removal from the recess of contaminants that may have a negative influence on the holding of the coil facility, an electrical and/or optical connection and/or a gas-tight connection to the gas feed.

The object-table-side and the coil-facility-side connecting facility may be embodied and arranged such that, when the connecting portion is held, at least one conductive projection as a coil-facility-side or object-table-side connecting device is pressed onto an assigned conductor strip extending in the longitudinal direction of the recess as an object-table-side or coil-facility-side connecting device to establish the electrical connection. In particular, it is possible for a pair including a projection and a conductor strip to be provided for each connection. The conductor strip may be flat and, for example, embodied as a litz wire, in particular made of copper. The projection may be a strip, a pin, or the like, or a row of pins or the like extending in the longitudinal direction of the recess.

It is possible for a plurality of the projections to be in contact with a conductor strip or vice versa. This may be possible if there is a requirement for it to be possible to use different coil facilities in a recess having a different number of projections or conductor strips, for example, to provide a different number of scanning channels. In this case, it may be advantageous for a control facility connected to the object-table-side connecting facility to identify which coil facility is being used and/or whether a plurality of projections is in contact with a conductor strip or vice versa. This is, for example, possible in that resistances between different conductive projections or conductive tracks are measured or in that a coil-facility-side identification facility is read out. Depending upon the coil facility detected or the detection of a duplicate occupancy, it is possible to deactivate individual object-table-side conductor strips or projections, e.g., so that they are not used to output control signals or to receive scan signals. In this case, these conductor strips or projections may be separated from scanning- or control-facility-side supply lines and hence lie in open status on a floating potential.

The object-table-side connecting device may be arranged on a side wall of the recess standing at an angle to the surface of the object table and extending in the longitudinal direction of the recess. This arrangement may enable a particularly reliable electrical and/or optical connection, in particular, if the connecting portion is pressed against the side wall, for example by a pressure hose.

At least one further pressure hose the extension of which may be varied by changing its filling pressure with a filling facility of the magnetic resonance facility may be arranged in the recess, wherein the coil-facility-side connecting device may be separated from the object-table-side connecting device by filling the further pressure hose. The separation may take place in that the connecting portion and hence the coil-facility-side connecting device is forced away from the object-table-side connecting device by the pressure hose during the filling of the pressure hose. The described separation of the connecting devices enables the avoidance of stresses on the connecting devices parallel to the respective contact surfaces that may result in scratching or tearing of the connecting devices.

It is possible to use two of the further pressure hoses, which are arranged symmetrically, for example above and below, with respect to the object-table-side connecting device. The two pressure hoses may be filled in a counter-rotating manner to support uniform disconnection of the connecting devices. The further pressure hoses may be used in conjunction with the above-described pressure hoses to clamp the connecting portion or also independently therefrom. The filling facility may be controlled by a control facility of the magnetic resonance facility. The filling facility may be embodied separately from or together with the above-described filling facilities.

The object table may have a plurality of recesses in each of which the connecting portion of the coil facility or a further connecting portion of the coil facility or at least one further coil facility may be held, wherein only parts of the recesses have an object-table-side connecting device. Recesses that do not have a connecting device may be considered as purely mechanical recesses exclusively use for holding coil facilities. It is, however, also possible for components to be arranged in the recesses without connecting devices that interact with the coil facility to provide further functionalities, for example the above-explained object-table-side gas feeds for filling gas cushions on the coil facility.

It is further proposed that the coil facility is embodied as semi-flexible, (e.g., plastically deformable), so that the coil facility may be deformable by the application of a force, wherein it retains its shape following the application of the force. The coil facility may therefore be bent into a desired form in which it remains autonomously, e.g., without the application of any external force. The deformation may be reversible, e.g., the coil facility may be returned to its original shape after deformation.

Hence it is easier to bring the at least one local coil into an optimized position for the magnetic resonance scan, in particular adapted more closely to the body of the individual patient.

To achieve semi-flexibility, the coil facility may include a semi-flexible housing and/or semi-flexible elements. In particular, the local coils may include semi-flexible electrical conductors of sufficient thickness to achieve a semi-flexible property.

It is also proposed that the at least one recess of the object table is, at least partially, arranged on one side relative to a longitudinal axis of the object table. In this case, the longitudinal axis of the object table may be parallel to the longitudinal axis of the at least one recess.

Hence, it is possible to dispense with a bilateral arrangement of two recesses within a portion along the longitudinal axis because a semi-flexible coil facility retains its shape of its own accord even without bilateral fixing.

In addition to the magnetic resonance facility, the disclosure relates to an object table for use in a magnetic resonance facility, wherein the object table is configured for mounting an object to be examined and for holding at least one coil facility embodied separately from the object table including at least one local coil, wherein the object table has at least one recess into which a connecting portion of the coil facility may be introduced and may be held there to hold the coil facility, wherein the connecting portion in the recess is guided displaceably along a longitudinal direction of the recess between different positions in which it may be held, wherein an object-table-side connecting device is arranged in the recess and configured such that, by the holding of the connecting portion in the recess, it establishes together with a coil-facility-side connecting device arranged on the connecting portion at least one electrical connection for the power supply for the coil facility and/or for signal transmission between the coil facility and the object table and/or at least one optical connection for signal transmission between the coil facility and the object table.

The disclosure also relates to a coil facility for use in a magnetic resonance facility including at least one local coil and at least one connecting portion, which is embodied such that it may be introduced into a recess of an object table and may be held there to hold the coil facility. The connecting portion in the recess is guided displaceably along a longitudinal direction of the recess between different positions in which it may be held. At least one coil-facility-side connecting device is arranged on the connecting portion and configured such that, when the connecting portion is held in the recess, it is coupled to an object-table-side connecting device arranged in the recess such that between the coil facility and the object table at least one electrical connection is established for the power supply for the coil facility and/or for signal transmission between the coil facility and the object table and/or at least one optical connection for signal transmission between the coil facility and the object table.

The object table and the coil facility may be developed by the features explained with respect to the magnetic resonance facility with the advantages mentioned there.

BRIEF DESCRIPTION OF THE DRAWINGS

Further advantages and details of the disclosure may be derived from the following exemplary embodiments and the associated drawings.

DETAILED DESCRIPTION

Figure 1:
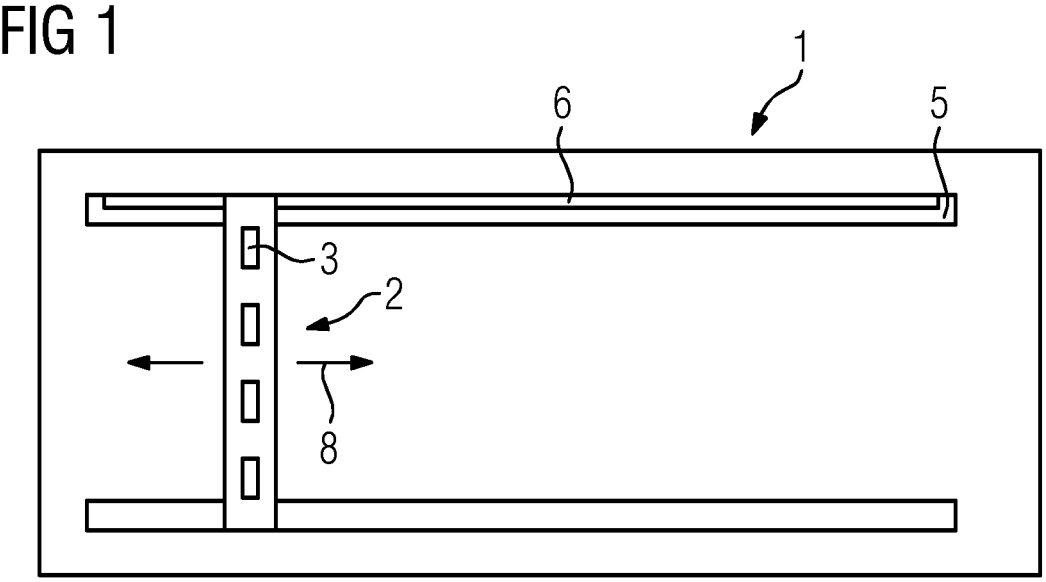
FIGS. 1 and 2 depict the interaction of an exemplary embodiment of an object table and an exemplary embodiment of a coil facility in an exemplary embodiment of a magnetic resonance facility.
Figure 2:
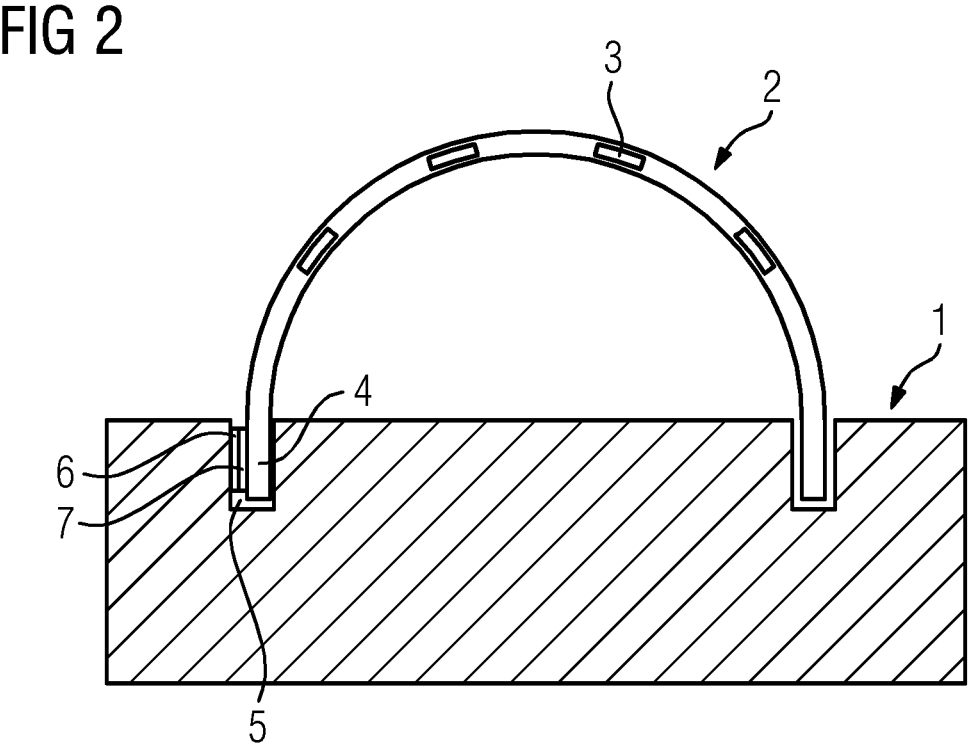

FIGS. 1 and 2 depict two schematic views of a part of a magnetic resonance facility including an object table 1 for supporting an object to be examined and a coil facility 2 embodied separately from the object table 1 arranged on the object table 1. The further components of the magnetic resonance facility, in particular a scanning and/or control facility, coils for the generation of magnetic fields and radio-frequency antennas for the irradiation of radio-frequency fields, are not shown for reasons of clarity. The coil facility 2 includes four local coils 3. It also has two connecting portions 4 each of which may be introduced into a recess 5 of the object table to hold the coil facility 2. The coil facility 2 is an elastic flexible coil facility 2, which, in its default state, is substantially straight. For arrangement on the object table 1, the coil facility 2 is bent into the arched shape depicted in FIG. 2 and its connecting portions 4 are introduced into the recesses 5 of the object table 1. In the exemplary embodiment depicted, the holding of the coil facility 2 on the object table 1 is exclusively achieved by the elastic resilience of the coil facility 2, which presses the connecting portions 4 against the walls of the recesses 5. This simple holding method was selected for reasons of clarity. Further holding options will be explained later with reference to other exemplary embodiments.

The connecting portions 4 are guided displaceably in the recesses 5 along a longitudinal direction of the object table 1 between different positions. This means the entire coil facility 2 is displaceable in the direction of the arrows 8. The described holding of the coil facility 2 permits continuous displacement of the connecting portions 4 and hence of the coil facility 2, wherein the connecting portions may be held at every position of this continuous displacement. Here, the elasticity of the coil facility 2 causes a coil-facility-side connecting device 7 arranged on the connecting portion 4 of the coil facility 2 to be pressed onto an object-table-side connecting device 6 arranged on a side wall of the recess 5.

A specific example of the design of these connecting devices 6, 7 will be explained later in detail with reference to FIG. 4 for a further exemplary embodiment. For example, projections may be provided on one connecting device 6, 7, for example in the form of pins or strips extending in the longitudinal direction of the recess 6, wherein said projections are pressed onto substantially flat conduction bands arranged on the other one of the connecting devices 6, 7 to establish one or more electrical connections.

This electrical connection may be used to supply power to electrical facilities (not shown) of the coil facility 2, for example active filters, amplifier circuits or multiplex circuits. Additionally, or alternatively, it is possible for electrical connections to be provided to guide scan signals of the coil facility 2 initially via the connecting devices 6, 7 to the object table and from there further to a scanning facility. The scan signals may be assigned individually to the local coils 3, however it is also possible for signals of several of the local coils 3 to be transmitted mixed or multiplexed as scan signals. Finally, it also possible for a control signal to be output via the electrical connections to components of the coil facility (not shown), for example to adjust the tuning of one of the local coils 3 or the like. Additionally, or alternatively to the electrical connection or electrical connections, the connecting devices 6, 7 may also provide an optical connection in that, for example, a coil-facility-side fiber-optic conductor may be coupled to an object-table-side fiber-optic conductor. The optical connection may be used for optical data transmission.

The use of longer recesses 5, which may hold the coil facility 2 in a plurality of positions, and the automatic contacting of the coil facility 2 via the connecting devices 6, 7 with arrangement and holding in the recesses 5 enable the coil facility to be arranged flexibly without additional cabling. In this case, it is possible for all the recesses 5 to have object-table-side connecting devices 6, however, it is also possible for only parts of the recesses 5 to have object-table-side connecting devices 6 as depicted in FIGS. 1 and 2.

In many applications, it may be desirable to reduce the clearance of the connecting portion 4 of the coil facility 2 in the recess 5 and/or to prevent the unintentional removal of the connecting portion 4 from the recess 5. This may be provided if, as will be explained in detail later, the coil facility 2 is additionally to be used to hold the object to be examined. One possibility for a holding of this kind is depicted in a further exemplary embodiment in FIG. 3. In this exemplary embodiment, the connecting portion 4 is initially inserted into the recess 5, the application of slight pressure causes a recess floor 9 that has sprung back to be pressed down. This enables the introduction of a coil-facility-side hook-shaped projection 11 along the guide strip 14 into the recess of an object-table-side hook-shaped projection 10. Hence, the springing back of the floor of the recess 9 causes the projection 11 to latch into the projection 10 in a disconnectable manner. Hence, the connecting portion 4 is held in the recess 5 but the holding is however relatively loose thus enabling the connecting portion 4 and hence the entire coil facility 2 to be displaced within the recess 5 with gentle guidance.

A pressure hose 12 arranged in the recess 5 may be used to establish a reliable contact between the object-table-side connecting device 6 and the coil-facility-side connecting facility 7 and minimize the clearance of the connecting portion 4 in the recess 5. The extension of the pressure hose 12 may be varied by changing its filling pressure with a magnet-resonance-facility-side filling facility (not shown). Increasing the pressure causes to the pressure hose 12 to extend and press the connecting portion 4 in FIG. 3 toward the right.

Figure 3:
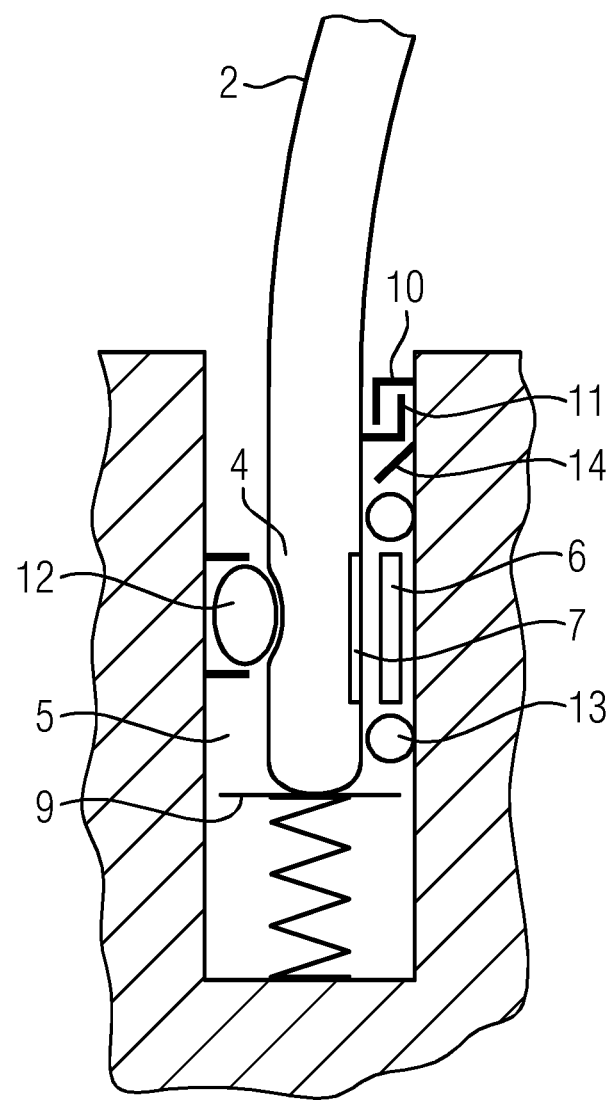
FIGS. 3 to 6 depict detailed views of further exemplary embodiments of magnetic resonance facilities.
Figure 4:
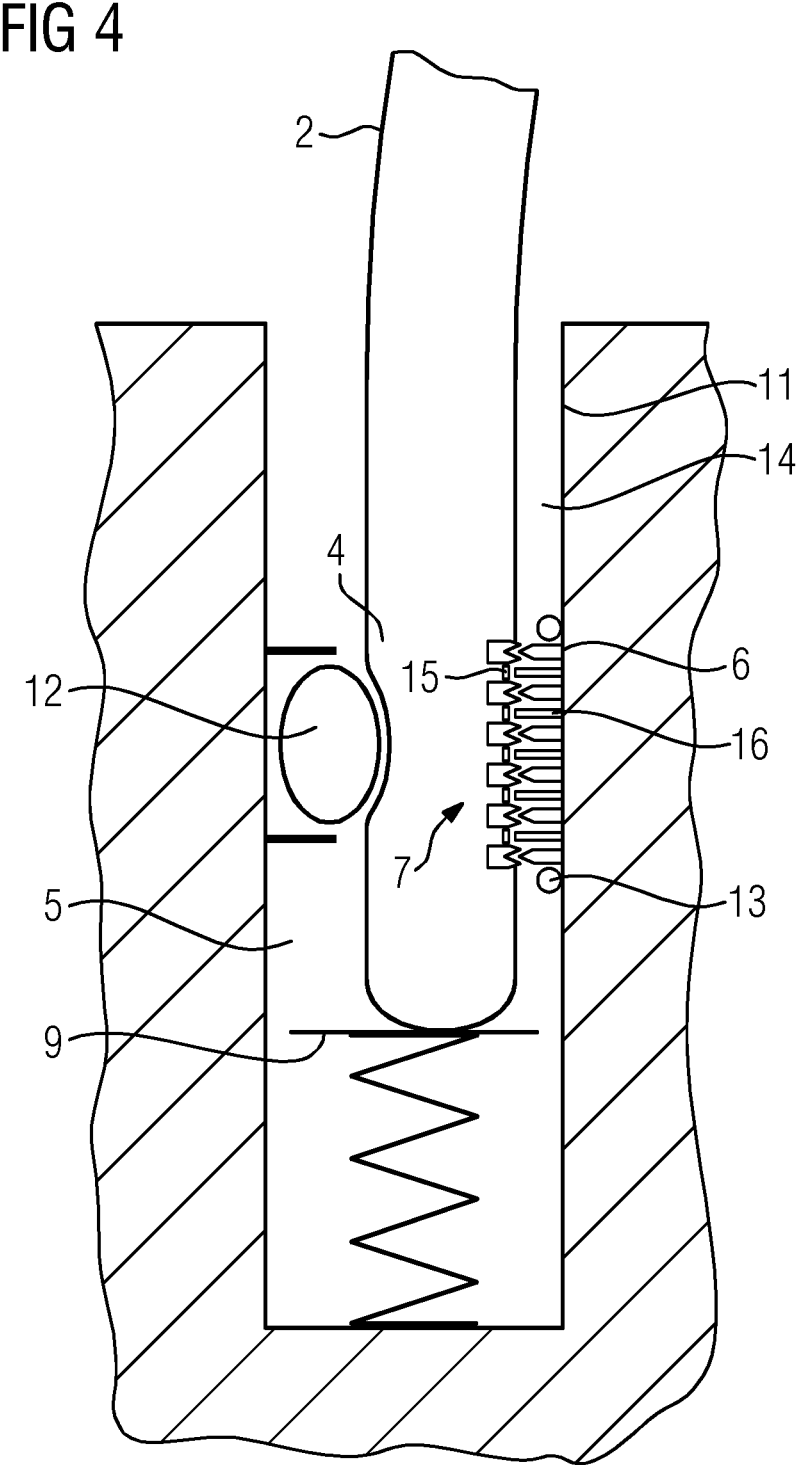

FIG. 4 depicts a detailed view of the connecting devices 6, 7 in FIG. 3. The object-table-side connecting device 6 has a plurality of identical projections 16, which may be embodied as pins or as strips extending perpendicular to the direction of the image. These lie opposite to substantially flat conductive tracks 15 on sides of the coil-facility-side connecting device 7. If the pressure hose 12 is now inflated, the conductive tracks 15 are pressed against the projections 16 and hence establish a plurality of electrical connections via which the coil facility may be supplied with current and/or control signals and/or scan signals may be transmitted.

To reduce stress on the connecting devices 6, 7 on the separation of connections due to forces in the connecting plane, the further pressure hoses 13 are also arranged in the recess 5. These are located above and below the object-table-side connecting device 6 and are filled with gas in a counter-rotating manner to separate the connecting devices 6, 7. The filling pressure of the pressure hose 12 is reduced at the same time. Hence, the further pressure hoses 13 are extended and the volume of the pressure hose 12 is reduced, thus causing the connecting portion 4 and hence the connecting device 7 to be pressed toward the left of the image. This enables gentle separation of the connecting devices 6, 7.

Figure 5:
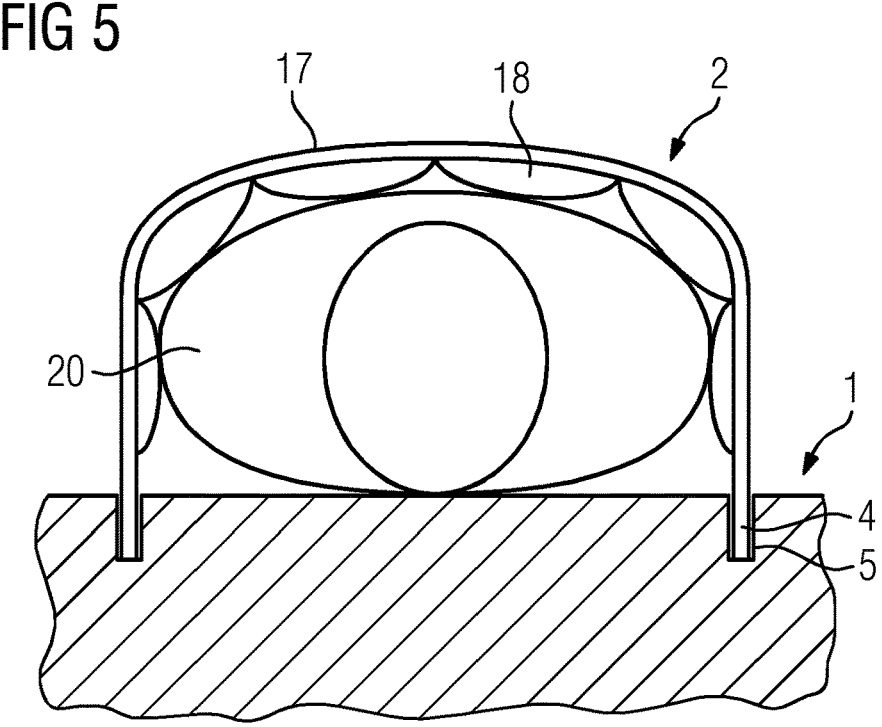
Figure 6:
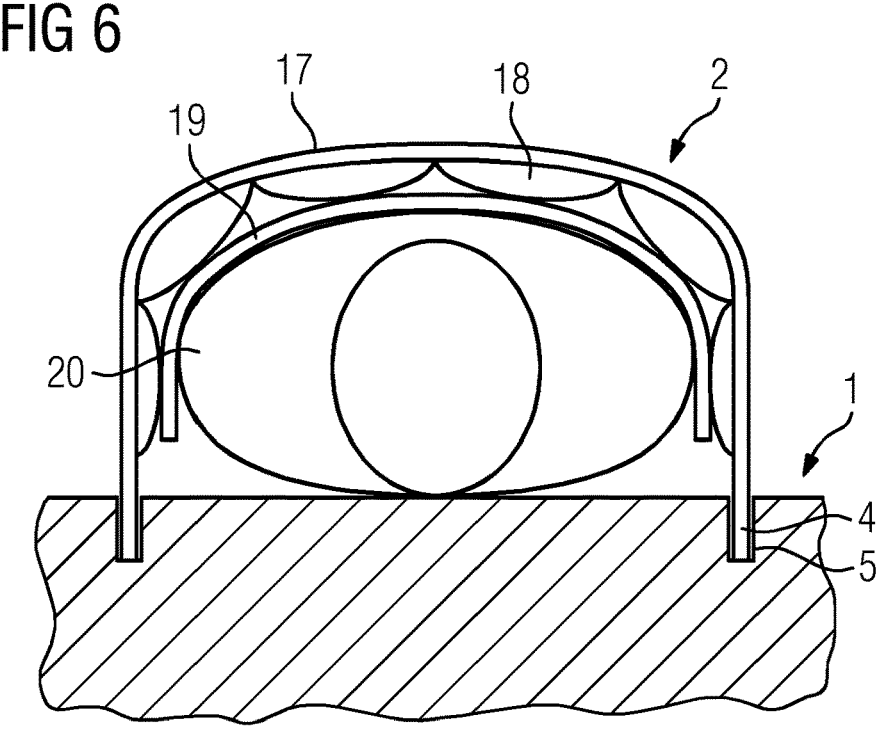

FIGS. 5 and 6 depict two exemplary embodiments of a coil facility 2 additionally configured to support or hold an object to be examined 20. In both exemplary embodiments, a rigid or elastic dimensionally stable support portion 17 is arranged on the connecting portions 4, which are held in the grooves 5, and endows the coil facility 2 with mechanical stability. As explained with respect to the previous exemplary embodiments, the connecting portions 4 and the grooves 5 are used, on the one hand, for mechanical holding and, on the other, for electrical contact with the coil facility 2. As will be explained later with reference to FIG. 7, this holding, may supply or remove gas, in particular compressed air, to change the extension of gas cushions 18 arranged on the support portion 17. Inflating the gas cushions 18 causes them to be pressed against the object to be examined 20 and hold or support said object in a stable position. In the exemplary embodiment depicted in FIG. 5, the local coils (not shown) are arranged in the support portion 17 and are hence kept at a distance from the object to be examined 20 by the gas cushions 18. This is a simple construction of the coil facility 2.

However, it is frequently desirable to bring the local coils as close as possible to the object to be examined 20 to achieve high scanning sensitivity. This is achieved by the exemplary embodiment depicted in FIG. 6 with which the local coils (not shown) are inserted into a support foil 19 arranged on the side of the gas cushion 18 facing the object to be examined 20 or the object table 1. If the gas cushions 18 have been substantially emptied, the local coils are held directly adjacent to the support portion 17. When the object to be examined 20 is supported on the object table 1 and the coil facility 2 is held in the recesses 5, the gas cushions 18 are inflated as a result of which, on the one hand, the object to be examined 20 is held thereby and, on the other, the support foil 19 and hence the local coils are brought as close as possible to the object to be examined to achieve optimum scanning quality.

Figure 7:
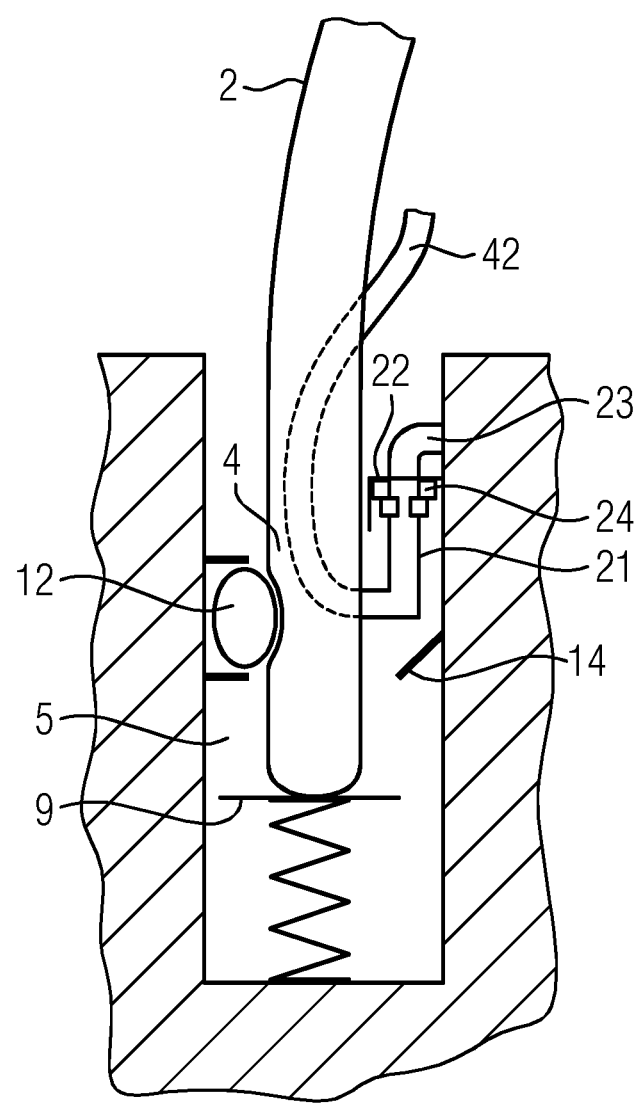
FIG. 7 depicts a detailed view of a gas feed for the exemplary embodiments depicted in FIGS. 5 and 6.

FIG. 7 depicts a possibility for a gas feed for the coil facilities 2 depicted in FIGS. 5 and 6 via one of the grooves 5. For reasons of clarity, the object-table-side connecting device 6 and the coil-facility-side connecting device 7 are not shown in FIG. 7. It is possible to implement the gas feed via one of the grooves 5 with no object-table-side connecting device exclusively used to hold one of the connecting portions 4 of the coil facility 2 and the gas feed. However, the gas feed may alternatively be integrated in the recess 5 that also provides the electrical and/or optical connection to the coil facility 2.

To enable a gas feed, the initial latching connection is implemented slightly differently than that depicted in FIG. 3. Instead of the hook-shaped projections 10, 11 depicted in FIG. 3, a hook-shaped pipeline forming a filling opening 21 is provided on the coil-facility side and a hook-shaped projection 22 including an object-table-side gas feed 23 includes on the object-table side. A sealing element 24, for example, a rubber seam is provided for gas-tight closure of the gas connection is provided at the outlet from gas feed 23. The hook-shaped filling opening 21 is connected to a gas hose 42 that may feed the gas supplied to the gas cushions (not shown).

Figure 8:
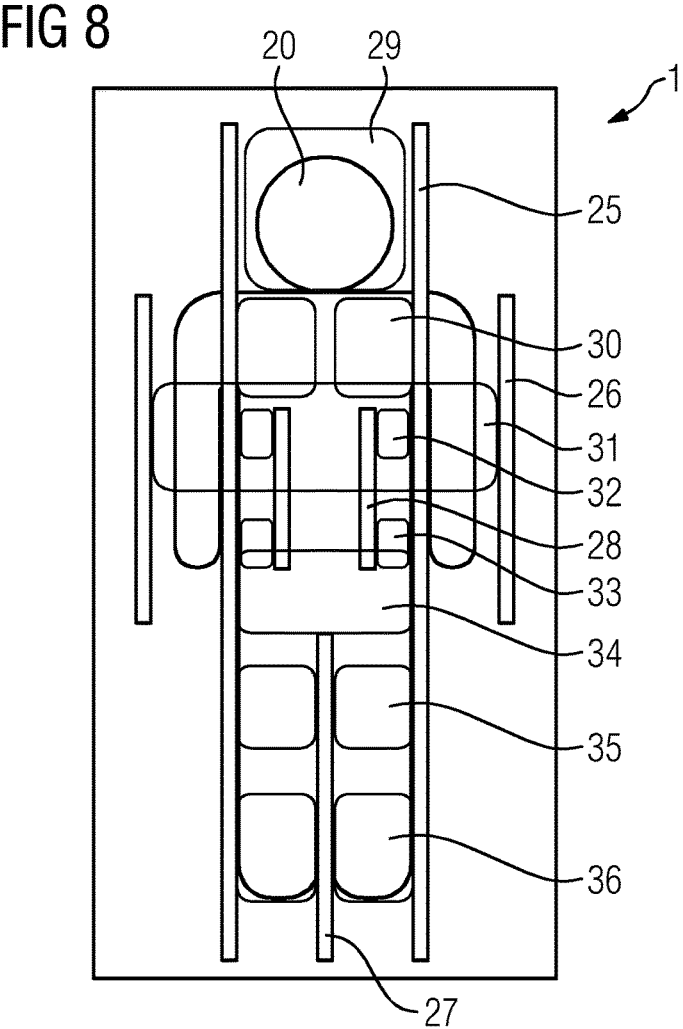
FIG. 8 depicts a further exemplary embodiment of an object table.

FIG. 8 depicts a further exemplary embodiment of an object table with a plurality of grooves 25, 26, 27, 28 as recesses. The grooves 25, 26 are electro-mechanical grooves, (e.g., recesses in which an object-table-side connecting device is provided), as explained with respect to the previous exemplary embodiments. The grooves 27, 28 are purely mechanical grooves, (e.g., recesses), in which no object-table-side connecting device is provided. Purely mechanical grooves are very simple to implement and may provide additional support points for specific scan geometries.

FIG. 8 depicts a plurality of positions 29-36 on which coil facilities may be arranged on the object to be examined 20 for imaging of different regions of the object to be examined 20. For imaging in the head and neck region, it is possible for the coil facility to be arranged at position 29 between the grooves 25. Shoulder imaging is possible in region 30 possible, wherein, to this end, the object to be examined 20 may be mounted asymmetrically. For holding in region 30, the coil facility may be held in the groove 25 exclusively by a single connecting portion. The grooves 26 enable a coil facility to be held as a torso array, for example in position 31. Imaging on the elbow or joint with asymmetric mounting of the object to be examined 20 is possible at positions 32 and 33 each of which depicts a coil arrangement between the grooves 25 and 28. A small torso array may be held between the two grooves 25 as a coil facility, for example, at position 34. When the coil facility is held between the grooves 25 and 27 imaging of the knee or foot or ankle is possible at the positions 35 and 36.

Figure 9:
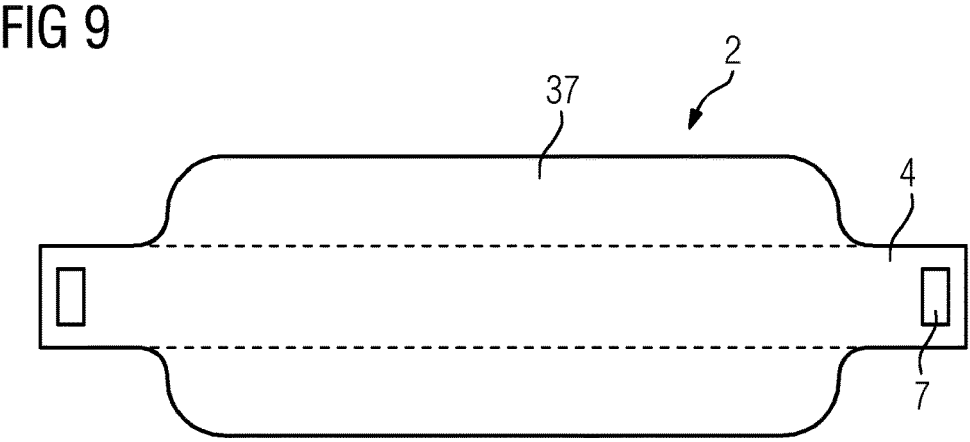
FIG. 9 depicts a further exemplary embodiment of a coil facility.

FIG. 9 depicts a further exemplary embodiment of a coil facility 2. This differs from the coil facility depicted in FIGS. 1 and 2 in that they have overlapping regions 37 extending beyond the extension of the connecting portion 4 in a widthwise direction of the coil facility 2. When two or more of the coil facilities are arranged in the same recesses such that their connecting portions 4 are immediately adjacent, these overlapping portions 37 enable the overlapping regions 37 to overlap at least partially thus enabling the quality of the imaging to be improved.

Figure 11:
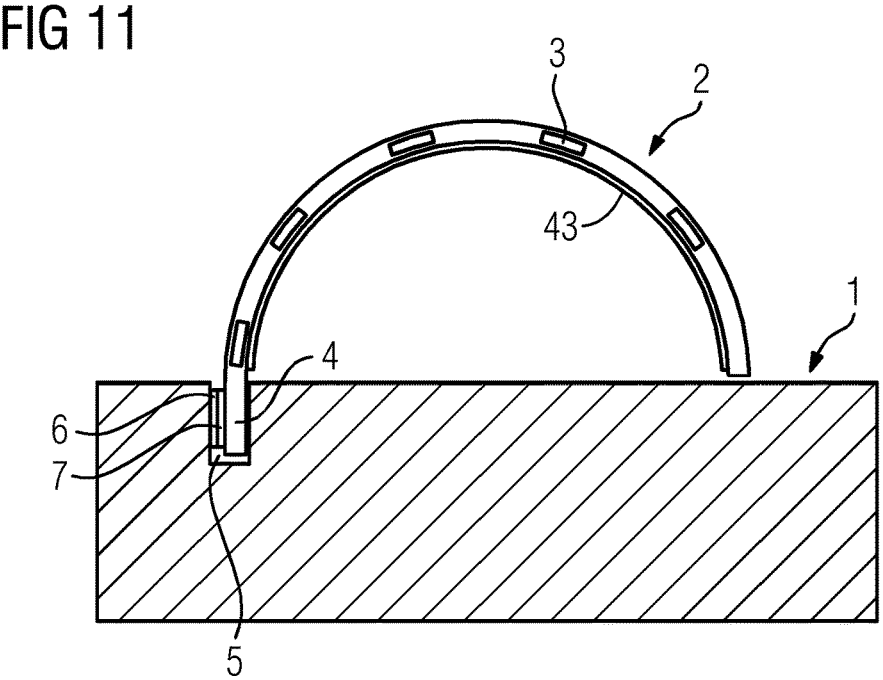
FIG. 11 depicts a further exemplary embodiment of magnetic resonance facilities with a unilateral arrangement.

FIG. 11 depicts a semi-flexible coil facility 2, which is arranged at least partially in a recess 5 of the object table 1 on one side relative to the longitudinal axis, on the left in the viewing direction. In this case, the coil facility 2 includes a semi-flexible element 43, holding the coil facility 2 in shape after deformation.

Figure 10:
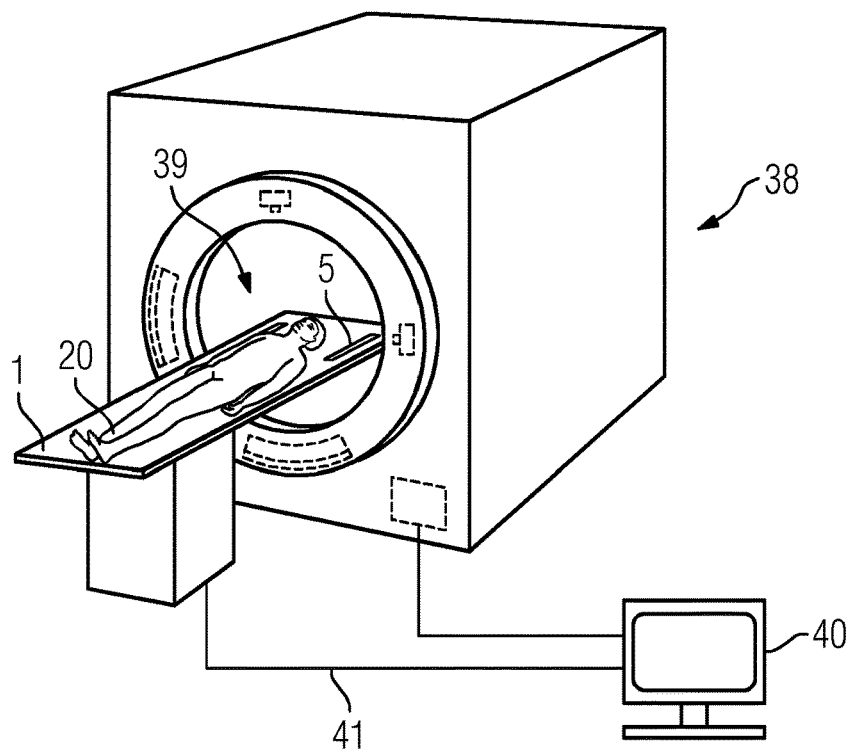
FIG. 10 depicts an overview of an exemplary embodiment of a magnetic resonance facility.

In one other possible portion, not shown here, a further recess 5 may also be arranged on the right of the longitudinal axis in the viewing direction. Hence, it is possible to cover a desired scanning region with a minimum number of recesses 5 and object-table-side connecting devices 6. FIG. 10 depicts an overview of an exemplary embodiment of a magnetic resonance facility 38. An object to be examined 20 may be moved into a tunnel 39 or magnetic resonance facility 38 on an object table 1. A scanning and control facility 40 is provided for controlling and the acquisition of scan data. One or more coil facilities (not shown), for example the coil facility 2 depicted in FIG. 9 may be held in the recesses 5 of the object table 1. As explained above, during the holding, at least one electrical and/or optical connection to the object table 1 is established that may be further extended by lines 41 external to the scanning region from the object table 1 to the scanning and control facility 40.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance facility comprising:
    an object table comprising a recess, the object table configured to support an object to be examined; and
    at least one coil facility embodied separately from the object table, the at least one coil facility comprising at least one local coil and at least one connecting portion, wherein the at least one connecting portion is configured to be introduced into the recess of the object table and configured to be held in the recess to hold the coil facility,
    wherein the connecting portion in the recess is guided displaceably along a longitudinal direction of the recess between different positions in which the connecting portion is configured to be held,
    wherein the recess and the connecting portion are configured for continuous displacement of the connecting portion in the recess,
    wherein the connecting portion is configured to be held at every position of the continuous displacement, and
    wherein at least one coil-facility-side connecting device is arranged on the connecting portion and, when the connecting portion is held in the recess, together with an object-table-side connecting device arranged in the recess, the at least one coil-facility-side connecting device establishes one or more of the following: an electrical connection for a power supply for the coil facility, an electrical connection for a signal transmission between the coil facility and the object table, or at least one optical connection for the signal transmission between the coil facility and the object table.

2. The magnetic resonance facility of claim 1, wherein the coil facility is elastic, flexible, or both elastic and flexible, and
wherein the coil facility has a connecting portion on each end of two opposite ends.

3. The magnetic resonance facility of claim 1, wherein the connecting portion is configured to be held in the recess by a detachable latching connection.

4. The magnetic resonance facility of claim 1, wherein a pressure hose is arranged in the recess, the pressure hose having an extension that is variable by changing a filling pressure with a filling facility of the magnetic resonance facility, and
wherein the connecting portion is configured to be clamped in the recess by increasing the filling pressure in the pressure hose.

5. The magnetic resonance facility of claim 1, wherein the coil facility comprises at least one gas cushion configured to fix the object to be examined, position the local coil, or fix the object to be examined and position the local coil, and
wherein an extension of the gas cushion is variable by changing a filling pressure with a filling facility of the magnetic resonance facility.

6. The magnetic resonance facility of claim 5, wherein the gas cushion is arranged between a support portion of the coil facility arranged on the connecting portion and the local coil or at least one of the local coils is arranged such that the relative position of the local coil with respect to the support portion is changeable by changing the filling pressure of the gas cushion.

7. The magnetic resonance facility of claim 5, wherein the gas cushion is Tillable with gas through a filling opening arranged on the connecting portion and, when the connecting portion is held in the recess, the gas cushion is connected in a gas-tight manner to an object-table-side gas feed through which the gas is configured to be fed from the filling facility to the gas cushion.

8. The magnetic resonance facility of claim 1, wherein the object-table-side and the coil-facility-side connecting device are embodied and arranged such that, when the connecting portion is held, at least one conductive projection as a coil-facility-side or object-table-side connecting device is pressed onto an assigned conductor strip extending in a longitudinal direction of the recess as an object-table-side or coil-facility-side connecting device to establish the electrical connection.

9. The magnetic resonance facility of claim 1, wherein the object-table-side connecting device is arranged on a side wall of the recess standing at an angle to a surface of the object table and extending in a longitudinal direction of the recess.

10. The magnetic resonance facility of claim 1, wherein at least one further pressure hose is arranged in the recess,
wherein an extension of the further pressure hose is variable by changing a filling pressure with a filling facility of the magnetic resonance facility, and
wherein the coil-facility-side connecting device is separable from the object-table-side connecting device by filling the further pressure hose.

11. The magnetic resonance facility of claim 1, wherein the recess comprises a plurality of recesses,
wherein each recess of which the connecting portion of the coil facility or a further connecting portion of the coil facility or at least one further coil facility is configured to be held, and
wherein only parts of the recesses have a respective object-table-side connecting device.

12. The magnetic resonance facility of claim 1, wherein the coil facility is semi-flexible.

13. The magnetic resonance facility of claim 12, wherein the recess of the object table is arranged at least partially on one side relative to a longitudinal axis of the object table.

14. An object table configured to be used in a magnetic resonance facility, the object table comprising:
a recess; and
an object-table-side connecting device arranged in the recess,
wherein the object table is configured to support an object to be examined and to hold at least one coil facility having at least one local coil,
wherein a connecting portion of the coil facility is configured to be introduced into the a recess, and is configured to be held within the recess to hold the coil facility,
wherein the connecting portion in the recess is configured to be guided displaceably along a longitudinal direction of the recess between different positions in which the connecting portion is configured to be held,
wherein the recess and the connecting portion are configured for continuous displacement of the connecting portion in the recess,
wherein the connecting portion is configured to be held at every position of the continuous displacement, and
wherein the object-table-side connecting device is configured such that, by the holding of the connecting portion in the recess, the object-table-side connecting device establishes together with a coil-facility-side connecting device arranged on the connecting portion one or more of the following: an electrical connection for a power supply for the coil facility, an electrical connection for a signal transmission between the coil facility and the object table, or at least one optical connection for the signal transmission between the coil facility and the object table.

15. A coil facility configured to be used in a magnetic resonance facility, the coil facility comprising:
at least one local coil; and
at least one connecting portion configured to be introduced into a recess of an object table and held in the recess to hold the coil facility,
wherein the connecting portion in the recess is configured to be guided displaceably along a longitudinal direction of the recess between different positions in which the connecting portion is configured to be held,
wherein the recess and the connecting portion are configured for continuous displacement of the connecting portion in the recess,
wherein the connecting portion is configured to be held at every position of the continuous displacement, and
wherein at least one coil-facility-side connecting device is arranged on the connecting portion and is configured that, when the connecting portion is held in the recess, the at least one coil-facility-side connecting device is coupled to an object-table-side connecting device arranged in the recess such that between the coil facility and the object table: an electrical connection is established for a power supply for the coil facility, an electrical connection is established for a signal transmission between the coil facility and the object table, at least one optical connection is established for a signal transmission between the coil facility and the object table, or a combination thereof.

* * * * *

UNITED STATES PATENT AND TRADEMARK OFFICE
CERTIFICATE OF CORRECTION

PATENT NO. : 10,444,306 B2
APPLICATION NO. : 15/485793
DATED : October 15, 2019
INVENTOR(S) : Katharina Hesels et al.

Page 1 of 1

It is certified that error appears in the above-identified patent and that said Letters Patent is hereby corrected as shown below:

In the Claims

Column 13, Line 41 "Tillable" – Should be replaced with – "fillable"

Signed and Sealed this
Fourteenth Day of January, 2020

Andrei Iancu
*Director of the United States Patent and Trademark Office*